(12) United States Patent
Lee et al.

(10) Patent No.: US 8,317,722 B2
(45) Date of Patent: Nov. 27, 2012

(54) METHOD AND DEVICE FOR HEARING TEST

(75) Inventors: Sang-Min Lee, Incheon (KR);
Kyoung-Ho Bang, Seoul (KR); Sung Hwa Hong, Seoul (KR); Sang-Ki Kang, Suwon-si (KR); Keun-Sup Lee, Seoul (KR); Jae-Hyun Kim, Suwon-si (KR); Hae-Mi Kim, Incheon (KR); Won-Jin Lim, Goyang-si (KR)

(73) Assignees: Samsung Electronics Co., Ltd., Suwon-si (KR); Inha-Industry Partnership Institute, Incheon (KR)

( * ) Notice: Subject to any disclaimer, the term of this patent is extended or adjusted under 35 U.S.C. 154(b) by 474 days.

(21) Appl. No.: 12/544,399

(22) Filed: Aug. 20, 2009

(65) Prior Publication Data
US 2010/0137739 A1    Jun. 3, 2010

(30) Foreign Application Priority Data
Aug. 20, 2008  (KR) .................... 10-2008-0081601

(51) Int. Cl.
*A61B 5/00*    (2006.01)
(52) U.S. Cl. ........................................... 600/559
(58) Field of Classification Search .................. 600/559
See application file for complete search history.

(56) References Cited

U.S. PATENT DOCUMENTS

| | | | | |
|---|---|---|---|---|
| 4,637,402 | A * | 1/1987 | Adelman | 600/559 |
| 7,018,342 | B2 * | 3/2006 | Harrison et al. | 600/559 |
| 7,223,245 | B2 * | 5/2007 | Zoth et al. | 600/559 |
| 7,704,216 | B2 * | 4/2010 | Margolis | 600/559 |
| 2006/0153396 | A1 * | 7/2006 | John | 381/60 |
| 2007/0129649 | A1 * | 6/2007 | Thornton et al. | 600/559 |
| 2008/0167575 | A1 * | 7/2008 | Cronin et al. | 600/559 |
| 2008/0310659 | A1 * | 12/2008 | Kim et al. | 381/316 |

* cited by examiner

*Primary Examiner* — Jeffrey G Hoekstra
(74) *Attorney, Agent, or Firm* — Stanzione & Kim, LLP

(57) ABSTRACT

A method of conducting a hearing test, and a device to perform the method, the method including configuring multiple test sound sets including multiple sound sources at each included audio frequency, wherein the sound sources, when sequentially arranged according to volume, have a uniform volume difference and a same frequency band, the uniform volume difference indicating a volume difference between neighboring sound sources, outputting the sound sources included in one of the multiple test sound sets, and determining and outputting a following test sound set according to a subject's input sound sources' number one or more times, and determining an auditory threshold of the subject regarding the audio frequency of the output test sound sets based on a result of the subject's input.

16 Claims, 11 Drawing Sheets

METHOD AND DEVICE FOR HEARING TEST

CROSS-REFERENCE TO RELATED APPLICATIONS

This application claims the benefit under 35 U.S.C. §119(a) of Korean Patent Application No. 10-2008-0081601, filed on Aug. 20, 2008, in the Korean Intellectual Property Office, the disclosure of which is incorporated herein by reference in its entirety.

BACKGROUND

1. Field of the Invention

The present general inventive concept relates to a method and device used in a hearing test, and more particularly to a method and device which can improve accuracy of the hearing test, compared to conventional measurements of a left/right auditory threshold.

2. Description of the Related Art

When a disorder occurs in a human ear, including any part of the outer ear, the middle ear, and the inner ear, a person cannot hear sounds very well. The resulting condition caused by this disorder is commonly referred to as being "hard of hearing." Such a condition of being hard of hearing may be divided into conductive hearing loss, sensorineural hearing loss, and mixed hearing loss. The conductive hearing loss occurs when eardrum-to-nerve transmission is not operative due to a weak cochlea or nerve function. The representative example of being hard of hearing due to conductive hearing loss is tympanitis. The sensorineural hearing loss occurs when an audible sound is not received due to a malfunction of an auditory nerve's own function, and representative examples of the sensorineural hearing loss includes sudden hearing loss, noise-induced hearing loss, presbycusis, or the like. The mixed hearing loss is caused by the factors of the conductive hearing loss and the sensorineural hearing loss, and may be caused by congenital or acquired developmental abnormality or ear diseases.

Nowadays, the number of patients suffering from being hard of hearing is increasing year after year. The increase in people suffering from noise-induced hearing loss is due to several factors, such as frequently being exposed to a high strength sound due to an increase of environmental noise, sound media, such as an mp3 player, etc. Also, the number of patients suffering from presbycusis and being hard of hearing due to chemical abuse or environmental pollution have steadily increased with years. At the present time, it is assumed that the hard of hearing population is about 10% of the world population, including Korea.

In general, a hearing test includes two methods: a descending method of carrying out measurement while gradually lowering the level from a high level (strength) at which a subject can clearly hear a sound, with respect to 6 frequency bands, that is, 250 Hz, 500 Hz, 1000 Hz, 2000 Hz, 4000 Hz, and 8000 Hz; and an ascending method of carrying out measurement while gradually increasing the level from a low level at which a subject cannot hear a sound. In determining a minimum auditory threshold, the descending method shows a lower result by about 5-10 dB (decibel), as compared to the ascending method. In these hearing test methods, a tester selects a frequency, sends the subject a test sound at the frequency, and obtains a result indicating whether the subject responded or not. In other words, the results indicate whether the subject heard the test sound at the respective test frequencies.

In a conventional hearing test, since it is possible to anticipate the loudness of the following sound within the same frequency, the accuracy of the test is diminished. Furthermore, the test requires considerable time in the processes in which the tester directly selects a frequency, controls the output of a test sound, and obtains a response from a subject. Also, such a long test time may hurt the subject's concentration, thereby reducing the test accuracy, and this reduction of test accuracy is more significant in patients suffering from presbycusis.

Meanwhile, there is another hearing test method, involving the automatic selection and application of test frequencies at uniform intervals, which can be carried out in a simpler manner. However, due to the regular interval between sounds, it is possible to expect a point of time when a test sound is output. Also, it is possible to approximate and expect a point of time when the following test sound is output by noting a point of time when a current output test sound ends. Moreover, the monotony by a uniform sound length may reduce concentration. Accordingly, an easier and more accurate hearing test method is urgently needed.

SUMMARY

Example embodiments of the present general inventive concept provide a method and device which can reduce the expectation of an output point of time, duration, and strength of a test sound during a hearing test, and can more accurately and more rapidly perform the test.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a method of conducting a hearing test with a hearing test device, the method including configuring multiple test sound sets including multiple sound sources at each included audio frequency, wherein the sound sources, when sequentially arranged according to volume, have a uniform volume difference and a same frequency band, the uniform volume difference indicating a volume difference between neighboring sound sources, outputting the sound sources included in one of the multiple test sound sets, and determining and outputting a following test sound set according to a subject's input sound sources' number one or more times, and determining an auditory threshold of the subject regarding the audio frequency of the output test sound sets based on a result of the subject's input.

The method may further include determining a number of the sound sources of each of the output test sound sets heard by the subject according to the subject's input sound sources' number.

The determining the auditory threshold of the subject may include determining and outputting, as the following test sound set, a test sound set having a smaller uniform level difference than the uniform level difference of a previously output test sound set, within a same frequency band as the previously output test sound set, according to the subject's input sound sources' number, receiving the subject's input sound sources' number regarding the following test sound set, and repeatedly performing the determining and outputting of the test sound sets, and the receiving of the subject's input sound sources' number, and determining the auditory threshold of the subject accordingly.

The determining the auditory threshold of the subject may include determining an ascending threshold indicating the subject's hearable minimum volume and a descending threshold indicating the subject's unhearable maximum volume from the sound sources included in the previously output test sound set and a test sound set having the same uniform level difference as the previously output test sound set within the same frequency band, according to the subject's input sound sources' number, determining a sound source having a mean volume between the ascending threshold and the descending threshold as the auditory threshold within the frequency band of the previously output test sound set in response to the uniform level difference of the previously output test sound set being a predetermined minimum level difference, and determining and outputting a test sound set comprising the ascending threshold and the descending threshold and having a smaller uniform level difference than the uniform level difference of the previously output test sound set as the following test sound set in response to the uniform level difference of the previously output test sound set being more than the predetermined minimum level difference, and re-determining the ascending threshold and the descending threshold according to the subject's input sound sources' number regarding the following test sound set.

If the subject's input sound sources' number is less than a number of the sound sources included in the test sound set corresponding to the input sound sources' number, and more than 0, the ascending threshold and the descending threshold may be determined from the sound sources included in the corresponding test sound set.

If the subject's input sound sources' number is 0, and it is determined that the subject heard all of the sound sources having higher volumes in the same frequency band than the sound sources included in the test sound set corresponding to the subject's input sound sources' number of 0, the determining the auditory threshold of the subject may further include determining, as the descending threshold, a highest volume sound source from the sound sources included in the test sound set corresponding to the subject's input sound sources' number of 0, and determining, as the ascending threshold, a sound source having a higher volume than the descending threshold by a uniform volume of the test sound set corresponding to the sound sources' number of 0.

If the subject's input sound sources' number equals a number of the sound sources included in the test sound set corresponding to the sound sources' number, and it is determined that the subject did not hear all of the sound sources having smaller volumes in the same frequency band than the volumes of sound sources included in the test sound set corresponding to the subject's input sound sources' number, the determining the auditory threshold of the subject may further include determining, as the ascending threshold, a lowest volume sound source from the sound sources included in the test sound set corresponding to the sound sources' number, and determining, as the descending threshold, a sound source having a lower volume than the ascending threshold by a uniform volume of the test sound set corresponding to the sound sources' number.

The determining the auditory threshold of the subject may further include outputting a predetermined null test sound set in response to the subject's input sound sources' number being more than a number of the sound sources included in the test sound set corresponding to the sound sources' number, and re-outputting the test sound set corresponding to the sound sources' number.

The determining the auditory threshold of the subject may further include determining and outputting a test sound set comprising the ascending threshold and the descending threshold, and having a smaller uniform level difference than the uniform level difference of the previously output test sound set, as the following test sound set in response to a volume difference between the sound sources corresponding to the ascending threshold and the descending threshold being more than the minimum volume difference, and then re-determining the ascending threshold and the descending threshold according to the subject's input sound sources' number regarding the following test sound set.

The output durations and output points of time of the respective sound sources included in the test sound sets may be randomly determined.

The a test start point of time and a test end point of time may be displayed on a screen in response to the test sound sets being output.

The foregoing and/or other features and utilities of the present general inventive concept may also be achieved by providing a device to conduct a hearing test, the device including a test sound storage unit to store multiple test sound sets comprising multiple sound sources at each included audio frequency, wherein the sound sources, when sequentially arranged according to volume, have a uniform volume difference and a same frequency band, the uniform volume difference indicating a volume difference between neighboring sound sources, and a controlling unit to configure the multiple test sound sets, output the sound sources included in one of the multiple test sound sets, determine and output a following test sound set according to a subject's input sound sources' number one or more times, and determine an auditory threshold of the subject regarding the audio frequency of the output test sound sets based on a result of the subject's input.

The controlling unit may determine a number of the sound sources of each of the output test sound sets heard by the subject according to the subject's input sound sources' number.

In determining the auditory threshold of the subject, the controlling unit may determine and output, as the following test sound set, a test sound set having a smaller uniform level difference than the uniform level difference of a previously output test sound set, within a same frequency band as the previously output test sound set, according to the subject's input sound sources' number, receive the subject's input sound sources' number regarding the following test sound set, and repeatedly perform the determining and outputting of the test sound sets, and the receiving of the subject's input sound sources' number, and determines the auditory threshold of the subject accordingly In determining the auditory threshold of the subject, the controlling unit may determine an ascending threshold indicating the subject's hearable minimum volume and a descending threshold indicating the subject's unhearable maximum volume from the sound sources included in the previously output test sound set, and a test sound set having the same uniform level difference as the previously output test sound set within the same frequency band, according to the subject's input sound sources' number, determine a sound source having a mean volume between the ascending threshold and the descending threshold as the auditory threshold within the frequency band of the previously output test sound set in response to the uniform level difference of the previously output test sound set being a predetermined minimum level difference, and determine and output a test sound set comprising the ascending threshold and the descending threshold and having a smaller uniform level difference than the uniform level difference of the previously output test sound set as the following test sound set in response to the uniform level difference of the previously output test sound set being more than the predetermined minimum level difference, and re-determines the ascending threshold and the descending threshold according to the subject's input sound sources' number regarding the following test sound set.

If the subject's input sound sources' number is less than a number of the sound sources included in the test sound set corresponding to the input sound sources' number, and more than 0, the ascending threshold and the descending threshold may be determined from the sound sources included in the corresponding test sound set.

If the subject's input sound sources' number is 0, and it is determined that the subject heard all of the sound sources having higher volumes in the same frequency band than the volumes of sound sources included in the test sound set corresponding to the subject's input sound sources' number of 0, the controlling unit, in determining the auditory threshold of the subject may determine, as the descending threshold, a highest volume sound source from the sound sources included in the test sound set corresponding to the subject's input sound sources' number of 0, and may determine, as the ascending threshold, a sound source having a higher volume than the descending threshold by a uniform volume of the test sound set corresponding to the sound sources' number of 0.

If the subject's input sound sources' number equals a number of the sound sources included in the test sound set corresponding to the sound sources' number, and it is determined that the subject did not hear all of the sound sources having smaller volumes in the same frequency band than the volumes of sound sources included in the test sound set corresponding to the subject's input sound sources' number, the controlling unit, in determining the auditory threshold of the subject, may determine, as the ascending threshold, a lowest volume sound source from the sound sources included in the test sound set corresponding to the sound sources' number, and may determine, as the descending threshold, a sound source having a lower volume than the ascending threshold by a uniform volume of the test sound set corresponding to the sound sources' number.

In determining the auditory threshold of the subject, the controlling unit may output a predetermined null test sound set in response to the subject's input sound sources' number being more than a number of the sound sources included in the test sound set corresponding to the sound sources' number; and re-output the test sound set corresponding to the sound sources' number.

In determining the auditory threshold of the subject, the controlling unit may determine and output a test sound set comprising the ascending threshold and the descending threshold, and having a smaller uniform level difference than the uniform level difference of the previously output test sound set, as the following test sound set in response to a volume difference between the sound sources corresponding to the ascending threshold and the descending threshold being more than the minimum volume difference, and then re-determine the ascending threshold and the descending threshold according to the subject's input sound sources' number regarding the following test sound set.

The output durations and output points of time of the respective sound sources included in the test sound sets may be randomly determined.

The foregoing and/or other features and utilities of the present general inventive concept may also be achieved by providing a method of conducting a hearing test, the method including outputting one or more previously configured test sound sets to a subject, at least one successive test sound set being newly configured according to an input of the subject regarding a current test sound set, and determining an auditory threshold of the subject according to the subject's input.

The previously configured test sound sets may include varying numbers of sound sources in a common frequency band.

The sound sources in any one of the previously configured test sound sets may have a uniform volume difference when sequentially arranged according to volume.

The sound sources in the successive test sound set may have a reduced uniform volume difference compared to the uniform volume difference of the sound sources in the current test sound set.

The previously configured and newly configured test sound sets may be automatically configured by a device through with the hearing test is conducted.

The method may also include repeating a previously output test sound set in response to the subject's input indicating the subject hearing more sound sources than are included in the current test sound set, and repeating the current test sound set some time after repeating the previously output test sound set.

The results of the current test sound set may not be stored in response to the subject's input indicating the subject hearing more sound sources than are included in the current test sound set.

The foregoing and/or other features and utilities of the present general inventive concept may also be achieved by providing a recording medium having recorded thereon a program to cause a computer to perform a method of conducting a hearing test, the method including outputting one or more previously configured test sound sets to a subject, at least one successive test sound set being newly configured according to an input of the subject regarding a current test sound set, and determining an auditory threshold of the subject according to the subject's input.

The foregoing and/or other features and utilities of the present general inventive concept may also be achieved by providing a method of conducting a hearing test, the method including automatically configuring and storing a plurality of test sound sets including varying numbers of sound sources, wherein intervals of time between outputting the sound sources vary among the test sound sets, and outputting the test sound sets to a subject to determine an auditory threshold of a subject according to an input from the subject.

The output times of the respective sound sources may vary in each respective test sound set.

The foregoing and/or other features and utilities of the present general inventive concept may also be achieved by providing an apparatus to conduct a hearing test, the apparatus including a configuring part to automatically configure a plurality of test sound sets including varying numbers of sound sources before starting the hearing test, and to configure new test sounds sets during the hearing test, and an outputting part to output one or more of the previously configured test sound sets to a subject, and to output at least one of the new test sound sets according to an input of the subject.

The configuring part may configure the test sound sets such that intervals of time between outputting the sound sources vary among the test sound sets.

The configuring part may configure the test sound sets such that output times of the respective sound sources vary in each respective test sound set.

The apparatus may further include a storage to store the previously configured test sound sets.

BRIEF DESCRIPTION OF THE DRAWINGS

These and/or other features and advantages of the present general inventive concept will become apparent and more readily appreciated from the following description of the embodiments, taken in conjunction with the accompanying drawings of which.

DETAILED DESCRIPTION OF THE EMBODIMENTS

Figure 1:
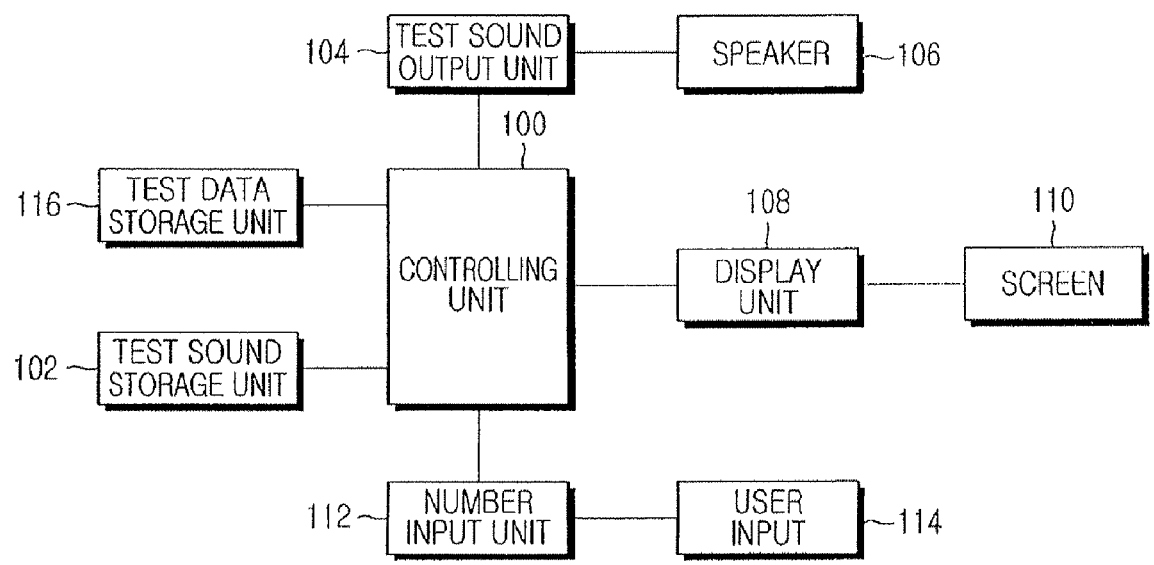
FIG. 1 is a view illustrating the configuration of a hearing test device according to an embodiment of the present general inventive concept.

Reference will now be made to exemplary embodiments of the present general inventive concept, examples of which are illustrated in the accompanying drawings, wherein like reference numerals refer to the like elements throughout. The embodiments are described below in order to explain the present general inventive concept by referring to the figures. In the following description of the present general inventive concept, detailed descriptions of known functions and configurations incorporated herein may be omitted to avoid making the subject matter of the present general inventive concept unclear.

Each test sound set according to the present general inventive concept may include sound sources having the same frequency band, in which when the sound sources are sequentially arranged and have volumes with a uniform dBSPL (Sound Pressure Level) or dBHL (Hearing Level) difference. A hearing test device according to embodiments of the present general inventive concept may include a test sound storage unit to store sound sources with different frequency bands or different volumes, a test sound output unit and a speaker to generate the sound sources; a display unit to indicate a start point of time and an end point of time when one test sound set is output and a screen to show the start and end points, a number input unit to receive the input of a subject's heard sound sources' number when the output of one test sound set ends, a button to input the number, and a test data storage unit to store a result whenever each test sound set is tested, and a controlling unit to control the above mentioned components.

According to the present general inventive concept, the controlling unit may output one test sound set by retrieving and outputting at least one of stored sound sources, change the kind of sound sources to be included in one test sound set in order to output another test sound set, and change an output time of each sound source. Also, after each test sound set is tested, the controlling unit may determine an auditory threshold, and initialize the data when the test is incorrect. Initializing the data refers to re-setting the corresponding results obtained with the test sound set in the event of receiving an incorrect input from the test subject, as will be explained in more detail later in this description.

Also, in order to configure a set including multiple sound sources having different volume levels within one frequency band to estimate a left/right auditory threshold, the method according to embodiments of the present general inventive concept may include randomly configuring the output intervals of respective sound sources to be included in one test sound set, the output durations of the respective sound sources, and the kinds of the respective sound sources, arranging configured test sound sets in a predetermined order or configuring them to be randomly output, displaying a screen indicating a start point of time and an end point of time and receiving the input of a subject's response under testing when the subject hears the configured test sound set, re-configuring a test sound set according to the response, and determining an auditory threshold by repeatedly outputting the re-configured test sound set and obtaining a corresponding subject's response.

FIG. 1 is a view illustrating the configuration of a hearing test device according to an embodiment of the present general inventive concept.

As illustrated in FIG. 1, the hearing test device according to the present general inventive concept may include a controlling unit 100, a test sound storage unit 102, a test sound output unit 104, a speaker 106, a display unit 108, a screen 110, a number input unit 112, a user input 114, and a test data storage unit 116.

The test sound storage unit 102 may store a test sound set including multiple sound sources with different volume levels in each audio frequency. Herein, sound sources included in one test sound set may have the same frequency band. Also, when the sound sources are arranged in descending order or in ascending order based on the volume, volume differences between neighboring sound sources may be equal. Such an equal volume difference is called a uniform volume difference. For example, a uniform volume difference may be 10 dB, 5 dB, or 2.5 dB, and may have a unit of SPL or HL. However, although volume differences between sequential sound sources included in each test sound set may be uniform, not all sound test sets have the same volume difference. For example, in one test sound set, sequential sound sources may have a uniform volume difference of 5 dBSPL, and in another test sound set, sequential sound sources may have a uniform volume difference of 10 dBSPL, and so on. The test sound storage unit 102 may store various kinds of sound sources with which to configure test sound sets.

The controlling unit 100 according to an embodiment of the present general inventive concept may configure the test sound set, and may store the test sound set in the test sound storage unit 102. According to an embodiment of the present general inventive concept, one test sound set may include sound sources having a uniform volume level difference. In other words, when the sound sources are arranged in descending order or in ascending order based on the volume, volume level differences between neighboring sound sources may be equal. Also, the number of sound sources included in one test sound set, the output duration of each sound source, and the output point of time of each sound source may be randomly determined. Then, the controlling unit 100 may retrieve and sequentially output the sound sources of a test sound set from the test sound storage unit 102 through the test sound output unit 104 and the speaker 106, and may display the start point of time and the end point of time of the test using the test sound set on the screen 110 via the display unit 108.

A subject can know the start point of time and the end point of time of one test sound set through the information displayed on the screen 110, and may input the number of heard sound sources by using the user input 114 when the output of the test sound set has completed. The user input 114 may be in the form of, for example, a button, a graphical user interface (GUI), etc. The number input unit 112 may receive the input of the subject through the user input 114 and send the input to the controlling unit 100. The number of sounds indicated as having been heard by the user in a test sound set may be referred to herein as the sound sources' number.

Figure 2:
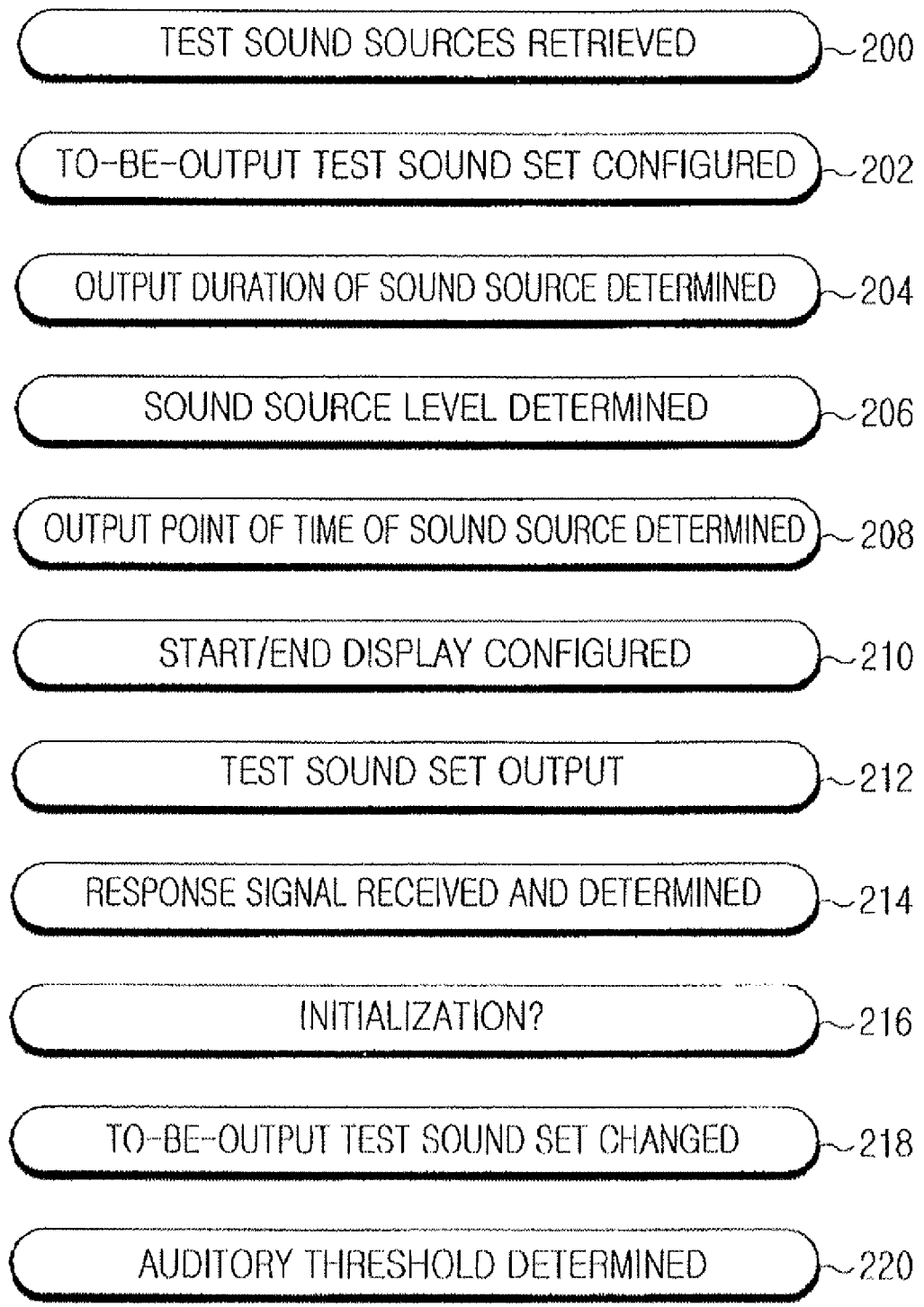
FIG. 2 is a view illustrating the configuration of a controlling unit according to an embodiment of the present general inventive concept.

The controlling unit 100 may store test result information based on the sound sources' number input by a user in the test data storage unit 116, and may reconfigure the test sound set. FIG. 2 is a view illustrating the operation of the controlling unit 100 according to an embodiment of the present general inventive concept.

As illustrated in FIG. 2, the controlling unit 100 according to the present general inventive concept may retrieve a plurality of test sound sources in operation 200, and may configure N (wherein N is a natural number) retrieved sound sources as one to-be-output test sound set in operation 202. When configuring one test sound set, the controlling unit 100 may select sound sources to be included in the set, may determine the output duration of each sound source in operation 204, may determine the sound source level and the uniform volume difference in operation 206, and may determine the output point of time of each sound source in operation 208. The controlling unit 100 may configure the display to indicate the start point of time and the end point of time of the entire hearing test, and the start point of time and the end point of time corresponding to the output test sound set in each hearing test, and display it on the screen 110 in operation 210, and may output the test sound set to be provided to the subject in operation 212. When a test response is received from the subject, the controlling unit 100 may determine the test result based on the test response in operation 214, and may determine whether to store the result in the test data storage unit 116 illustrated in FIG. 1 or to initialize the data in operation 216. The controlling unit 100 may change a test sound set to be output in operation 218, and may repeatedly perform the above described operations while determining an auditory threshold based on the test results of each test sound set in operation 220. The auditory threshold is a value which is estimated as a subject's hearable minimum volume within any frequency band. Also, whenever each test sound set is output, the controlling unit 100 may output the test sound set several times in order to objectively determine the test. These processes will be described in more detail later in the description of FIGS. 7-8B.

Figure 3:
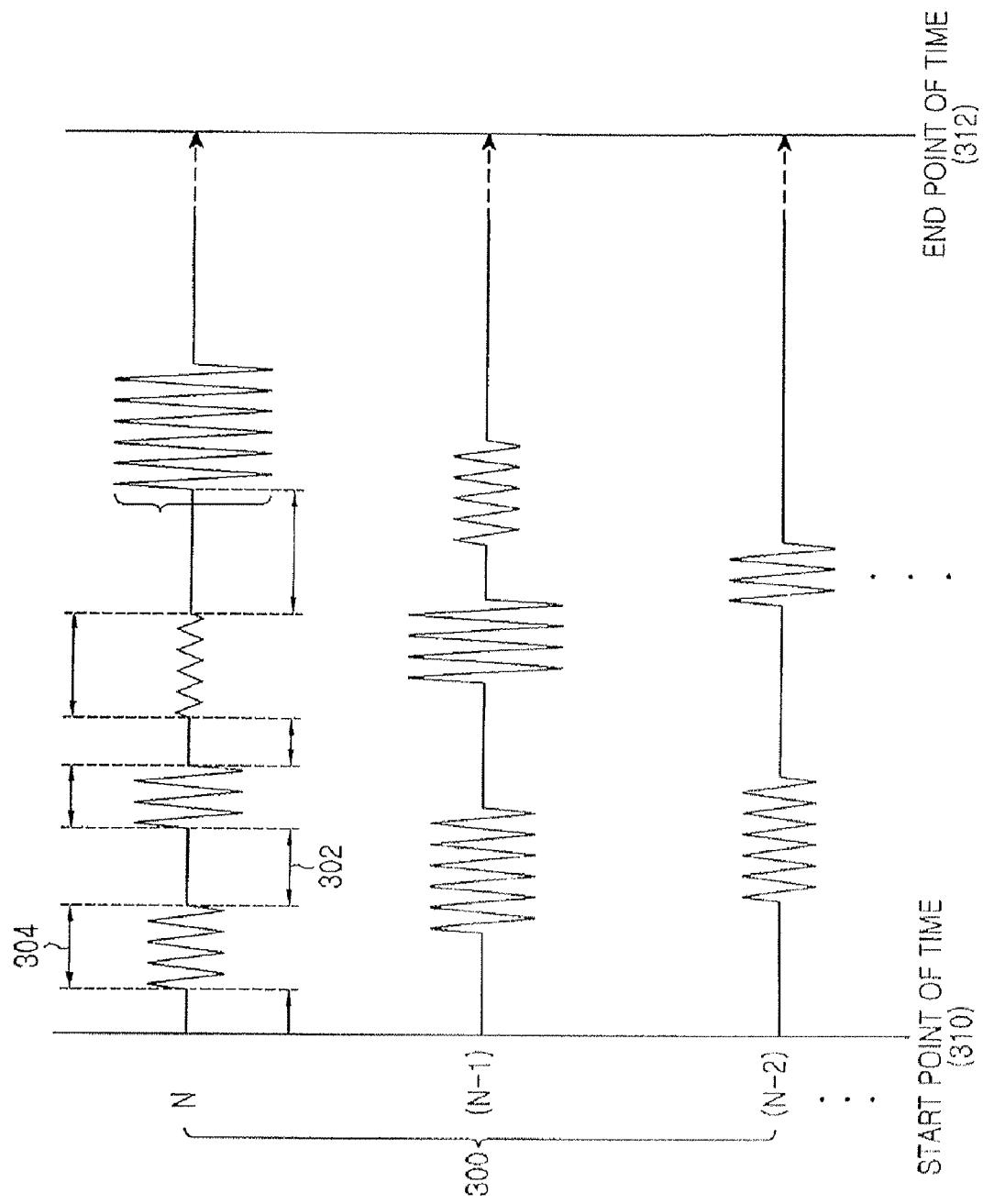
FIG. 3 is a view illustrating the configuration of a test sound set according to an embodiment of the present general inventive concept.

FIG. 3 is a view illustrating multiple test sound sets 300 according to an embodiment of the present general inventive concept. Referring to FIG. 3, the test sound sets 300 may respectively include N sound sources, (N−1) sound sources, and (N−2) sound sources. Herein, sound sources included in one test sound set may have the same frequency band, and sequential volume levels with a predetermined difference. In other words, when sound sources included in one test sound set are sequentially arranged based on volume level, volume level differences between neighboring sound sources may be uniform, for example, 10 dBSPL or 5 dBSPL. The number of sound sources included in each test sound set is randomly determined, and some test sound sets may have the same number of sound sources.

For example, a test sound set corresponding to a frequency band of 250 Hz may include three sound sources, three sound sources, and four sound sources in descending order from the largest strength, and a test sound set corresponding to a frequency band of 500 Hz may include four sound sources, two sound sources, and four sound sources in descending order from the largest strength. In order to reduce the test time of a hearing test, one test sound set may be configured to include at least two sound sources. These variations prevent the number of test sounds to be output in one set from being expected during the test. In other words, the variations can prevent the user from predicting the test sounds.

Referring to FIG. 3, in a test sound set a waiting time from a test start point of time 310 until a first sound source may be set, and an output interval 302 between sound sources may be randomly adjusted by M±αn seconds (wherein M and α are positive rational numbers, and n is a natural number) whenever each test sound set is output. Herein, M indicates a base waiting time, and α plays a role of increasing or decreasing the base waiting time. For example, if the base waiting time M is 1 second, and α is 0.5 seconds, the output interval 302 between sound sources may be 0.5 seconds, 1 second, 1.5 seconds, 2 seconds, etc. Through this adjustment, when a test sound set is provided to a subject during a test, the output point of time of the first sound source is varied, thereby inhibiting the expectation of the output time of the first sound source, and the interval between the output sound sources is varied, thereby inhibiting the expectation of the output point of time at which the following sound source will be output. Meanwhile, the end point of time 312, which indicates that the test of one test sound set has completed, may be the same in all test sound sets. For example, if the test of one test sound set requires 10 seconds, the entire test time of each of other test sound sets may be desired to be 10 seconds no mater how many sound sources are included in each test sound set. This aids in preventing a subject from estimating the number of test sounds during the test.

The output duration 304 of each sound source included in the test sound set may be randomly adjusted by L±βn (wherein L and β are positive rational numbers, and n is a natural number) whenever N sound sources are output. Herein, L indicates a base output duration time, and β plays a role of increasing or decreasing the base output duration time. For example, if the base output duration time L is 0.8 seconds, and β is 0.3 seconds, the output duration may be adjusted to be 0.5 seconds, 0.8 seconds, 1.1 seconds, etc. If the output durations of sound sources are uniform, the resulting monotony may hurt the concentration of the subject, thereby reducing the test accuracy during the test. Also, the expectation of the output end point of time of the sound source allows the subject to approximately expect the output point of time of the next sound source. Therefore, the adjustment of the output duration aids in preventing these problems.

Figure 4A:
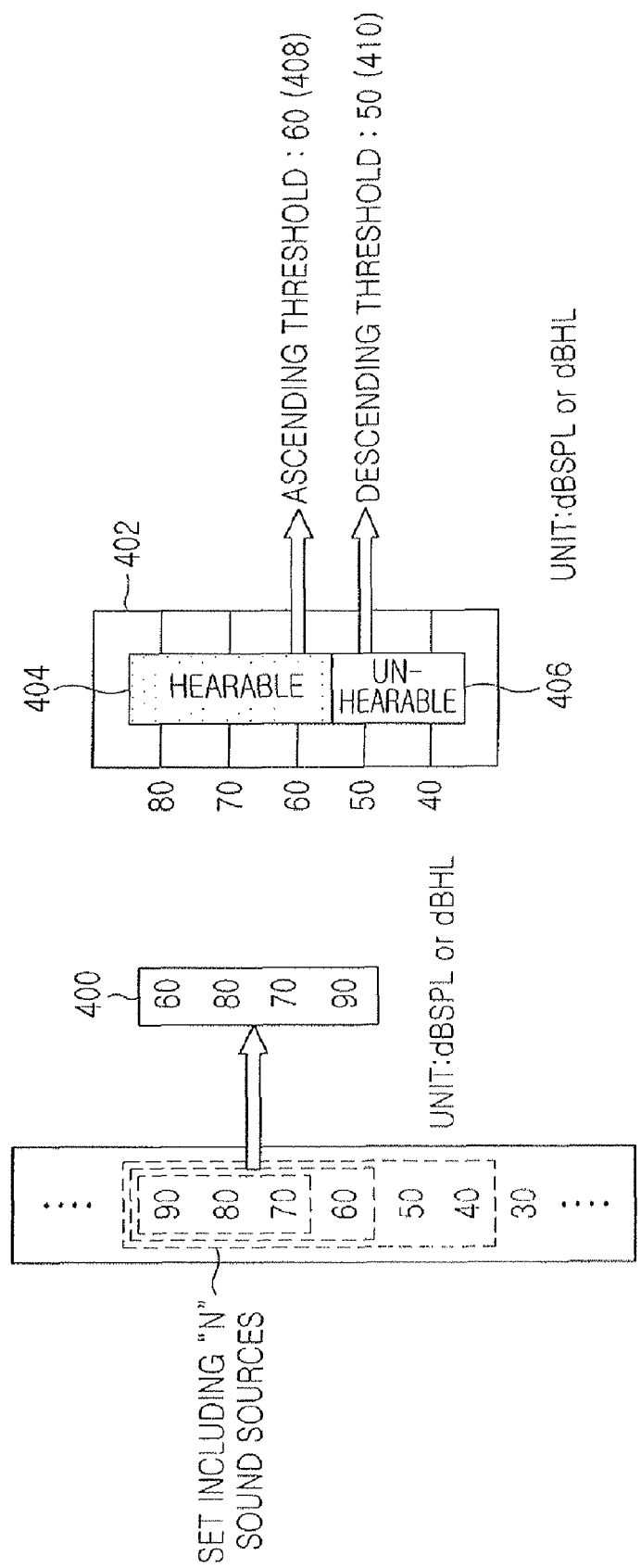
FIGS. 4A and 4B are views illustrating the process of determining an ascending threshold, a descending threshold, and an auditory threshold according to an embodiment of the present general inventive concept.
Figure 4B:
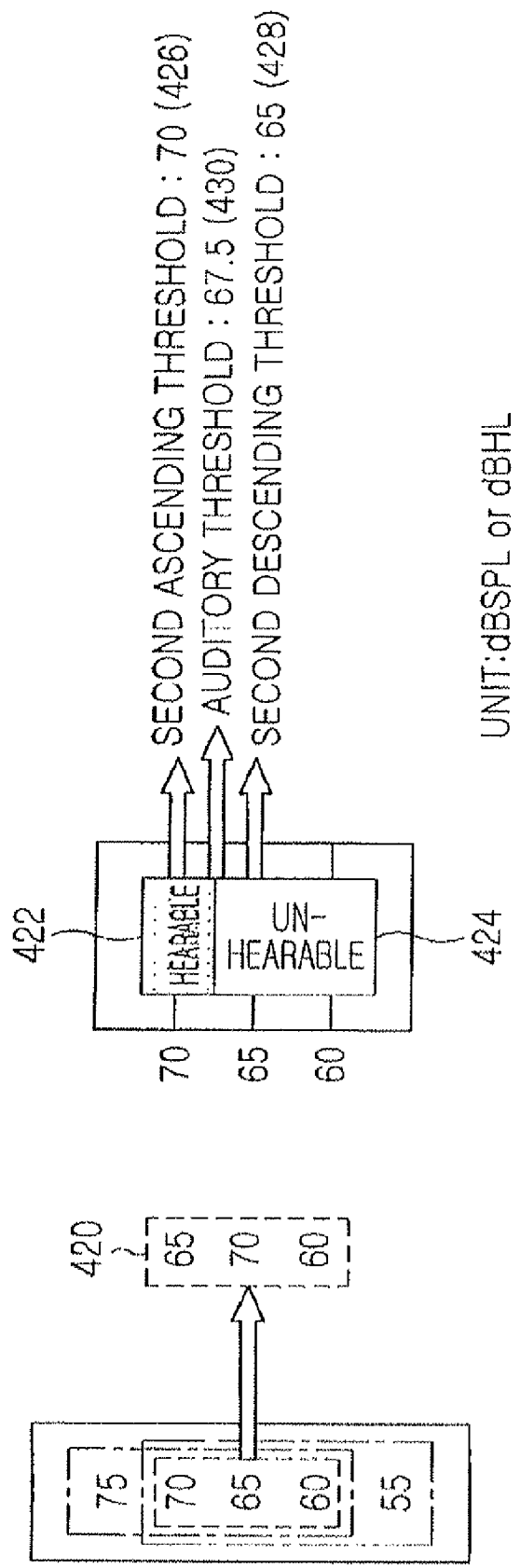

FIGS. 4A and 4B are views illustrating a process of determining an ascending threshold, a descending threshold, and an auditory threshold, according to an embodiment of the present general inventive concept. A test sound set output at an initial stage of a test may include N sound sources having sequential volume levels with a uniform difference (e.g., 10 dBSPL) within the same frequency band. Herein, the lowest volume level and the highest volume level are not separately set according to frequency bands. For example, a test sound set may include sound sources of 90 dBSPL, 80 dBSPL, and 70 dBSPL, or include sound sources of 70 dBSPL, 60 dBSPL, 50 dBSPL, and 40 dBSPL. Also, the output order of the sound sources included in the test sound set may be randomly determined. For example, referring to FIG. 4A, the output order of a first test sound set 400 including sound sources of 90 dBSPL, 80 dBSPL, 70 dBSPL, and 60 dBSPL may be randomly set, for example, in order of 60 dBSPL, 80 dBSPL, 70 dBSPL, and 90 dBSPL.

However, in order to efficiently utilize a test time, options regarding inquiries about whether the subject's hearing capability is, for example, good, average, or poor may be added, so that an appropriate test sound set can be initially output. When the subject's hearing capability is good, the controlling unit 100 may initially configure and output a test sound set with low levels in each frequency band. When the subject's hearing capability is poor, the controlling unit 100 may initially configure and output a test sound set with high levels in each frequency band, and when the subject's hearing capability is average, the controlling unit 100 may initially configure and output a test sound set with middle levels in each frequency band.

Hereinafter, after a test sound set is output, the process of determining an ascending threshold and a descending threshold according to a subject's response, configuring a new test sound set according to the determined ascending threshold and descending threshold, and finally determining an auditory threshold will be described. The ascending threshold is a minimum level sound source from among the subject's hearable sound sources in the output test sound set. The descending threshold is a maximum level sound source from among the subject's unhearable sound sources in the output test sound set. When the ascending threshold and the descending threshold are determined in a test sound set including a minimum uniform volume difference between sequential sound sources, the auditory threshold may be determined, and the minimum volume difference may be previously determined according to a person's general hearing capability. In the following description, the case with a minimum volume difference of 5 dBSPL will be described.

Hereinafter, the process of determining an ascending threshold and a descending threshold will be described by exemplifying a second test sound set 402 including sound sources having sequential volume levels with a difference of 10 dBSPL, as illustrated in FIG. 4A. The second test sound set 402 includes sound sources of 80 dBSPL, 70 dBSPL, 60 dBSPL, 50 dBSPL, and 40 dBSPL. It is assumed that after sound sources of the second test sound set 402 are output in descending order based on the volume, the subject's input sound sources' number is less than the number of output sound sources, and more than 0 (e.g., 3). Through such a response of the subject, the test sound set may be divided into a hearable portion 404 including sound sources of 80 dBSPL, 70 dBSPL, and 60 dBSPL, and an unhearable portion 406 including sound sources of 50 dBSPL and 40 dBSPL. In the hearable portion 404, the lowest level of 60 dBSPL is determined as an ascending threshold 408, and in the unhearable portion 406, the highest level of 50 dBSPL is determined as a descending threshold 410.

When the ascending threshold and the descending threshold are approximately determined in this way, a new test sound set including the ascending threshold 408 and the descending threshold 410, and sound sources having sequential levels with a smaller volume level difference than that between sound sources of the previous test sound set is configured. For example, when the volume level difference of the first test sound set is 10 dBSPL, the volume level difference of the following second test sound set may be configured to be 5 dBSPL.

Hereinafter, another example will be described with reference to FIG. 4B. For this example, it is assumed that a test sound set including 60, 80, 50, and 70 dBSPL within the same frequency band were output to a subject, and the subject input a response of "2." In such a case, 80 dBSPL and 70 dBSPL are determined to be the hearable portion, and 60 dBSPL and 50 dBSPL are determined to be the unhearable portion. Also, 70 dBSPL is determined to be the ascending threshold, and 60 dBSPL is determined to be the descending threshold. Then, a new test sound set is configured and output as a second test sound set 420, which may include sound sources of 70 dBSPL, 65 dBSPL, and 60 dBSPL, together with other sound sources with volume levels higher than the ascending threshold and lower than the descending threshold by 5 dBSPL. In other words, the third test sound set 420 may include "N" sound sources from among 75 dBSPL, 70 dBSPL, 65 dBSPL, 60 dBSPL, and 55 dBSPL. In configuring the N sound sources, in order to accurately carry out a test, the test sound set may include two or more sound sources, and preferably, though not necessarily, may include sound sources between the ascending threshold and the descending threshold.

According to this embodiment of the present general inventive concept, the second test sound set 420 includes sound sources of 70 dBSPL, 65 dBSPL, and 60 dBSPL. Then, after the output of the second test sound set 420, an ascending threshold and a descending threshold are secondly determined according to the subject's input sound sources' number, and then a value obtained by dividing the interval between the ascending and descending thresholds by 2.5 dBSPL is finally determined as an auditory threshold.

For example, after the output of the second test sound set 420, when a response of "1" is received from the subject, it is determined that the subject heard the sound source of 70 dBSPL, and did not hear the sound sources of 65 dBSPL and 60 dBSPL. In other words, the sound source of 70 dBSPL is determined to be the hearable portion 422, and the sound sources of 65 dBSPL and 60 dBSPL are determined to the unhearable portion 424. Accordingly, the sound source of 70 dBSPL is determined to be a second ascending threshold 426, a sound source of 65 dBSPL is determined to be a second descending threshold 428, and the mean value between them, which is 67.5 dBSPL, may be determined as a final auditory threshold 430.

Figure 5:
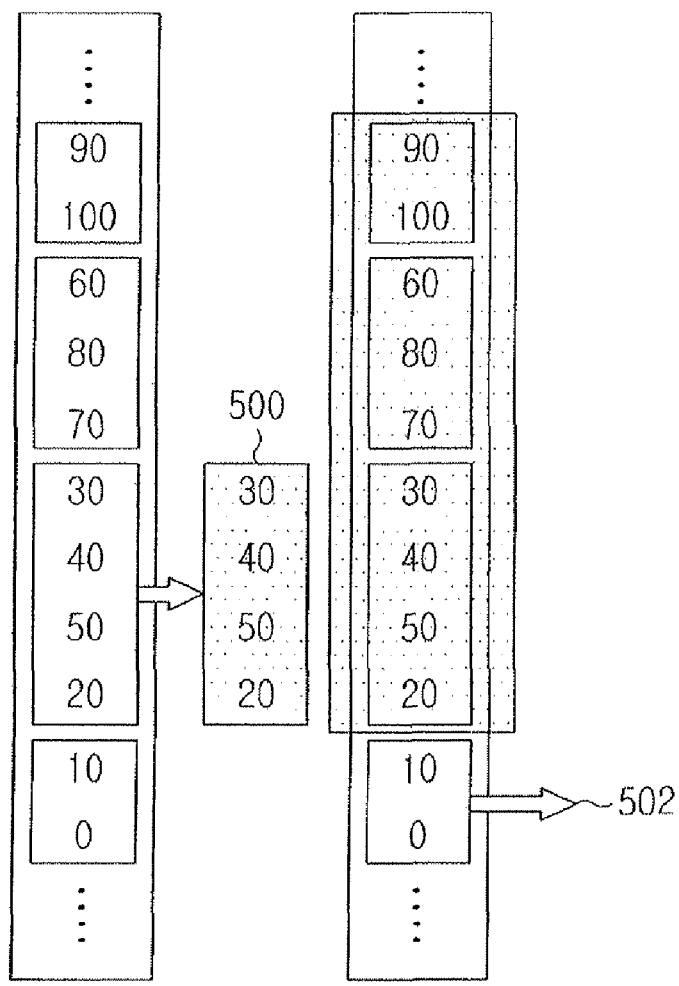
FIG. 5 is a view illustrating the configuration of a test sound set based on a subject's response according to an embodiment of the present general inventive concept.
Figure 5:
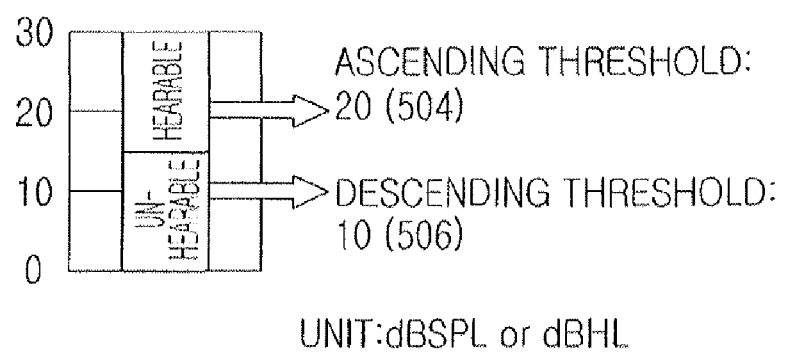

In the above described embodiment, a subject's response is more than 0, and is less than the number of output sound sources. Hereinafter, a case in which a subject's response is either equal to the number of output sound sources, or is 0, will be described with reference to FIG. 5, which is a view illustrating the configuration of a test sound set based on a subject's response according to an embodiment of the present general inventive concept After the output of one test sound set, if the subject's input sound sources' number is equal to the number of output sound sources, the following test sound set may include sound sources other than the sound sources having higher volumes than those of the sound sources included in the previously output test sound set.

For example, after the output of a test sound set 500 including sound sources of 30 dBSPL, 40 dBSPL, 50 dBSPL, and 20 dBSPL within any one frequency band, and when the sound sources' number input from the subject is 4, it may be determined that the subject heard all of the sound sources. Then, it may be assumed that the subject can hear sound sources with higher volume levels than those of the output sound sources just administered to the subject. Accordingly, a second test sound set 502 may include sound sources of 10 dBSPL and 0 dBSPL, but not sound sources with higher volume levels (that is, 60 dBSPL, 70 dBSPL, 80 dBSPL, 90 dBSPL, and 100 dBSPL) than those of the sound sources included in the previous test sound set 500, within the corresponding frequency may be configured and output.

If the fifth test sound set 502 is administered to the subject, and the sound sources' number input from the subject is 0, it may be determined that the subject heard all of the previous test sound set 500, and did not hear any of the second test sound set 502. Accordingly, the highest level sound source of 10 dBSPL in the second test sound set 502 is determined to be a descending threshold 506, and another sound source with a higher level than the descending threshold, by 10 dBSPL, is determined to be an ascending threshold 504. This is because sound sources included in the second test sound set 502 have a level difference of 10 dBSPL.

After the output of one test sound set, if the response from the subject is 0, the following randomly output test sound set may include sound sources other than the sound sources corresponding to the current test sound set and sound sources with lower levels than those of the sound sources corresponding to the current test sound set. In other words, after the output of the test sound set 500, if the response from the subject is 0, it may be assumed that the subject cannot hear the lower level sound sources because the subject did not hear any of the sound sources in the test sound set 500. Accordingly, from among test sound sets including other sound sources, such as, for example, 70 dBSPL, 80 dBSPL, 90 dBSPL, and 100 dBSPL, within a corresponding frequency, and not including sound sources included in the test sound set 500 and sound sources with lower levels (that is, 0 dBSPL, and 10 dBSPL), one test sound set is selected and output.

Meanwhile, in the case in which the subject's input sound sources' number is 0 after the output of one test sound set, and the subject's input sound sources' number is equal to that of all the sound sources of the following output test sound set, it may be determined that the subject did not hear any of the first test sound set, and heard all of the following test sound set. Accordingly, the lowest level sound source in the following test sound set may be determined to be an ascending threshold, and a sound source with a lower level than the ascending threshold, by 10 dBSPL, may be determined to be a descending threshold.

Figure 6A:
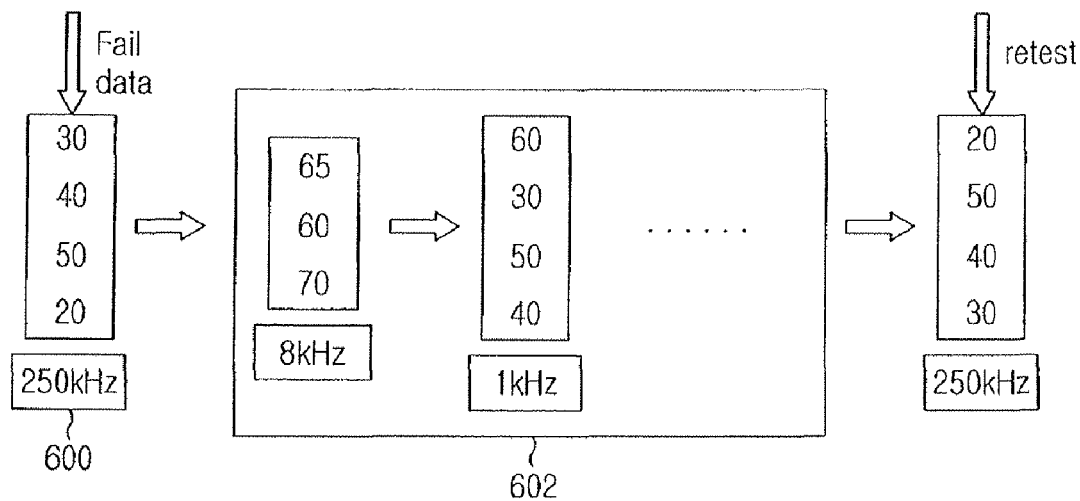
FIGS. 6A to 6C are views illustrating the process of determining an ascending threshold and a descending threshold based on a subject's incorrect response, according to an embodiment of the present general inventive concept.
Figure 6B:
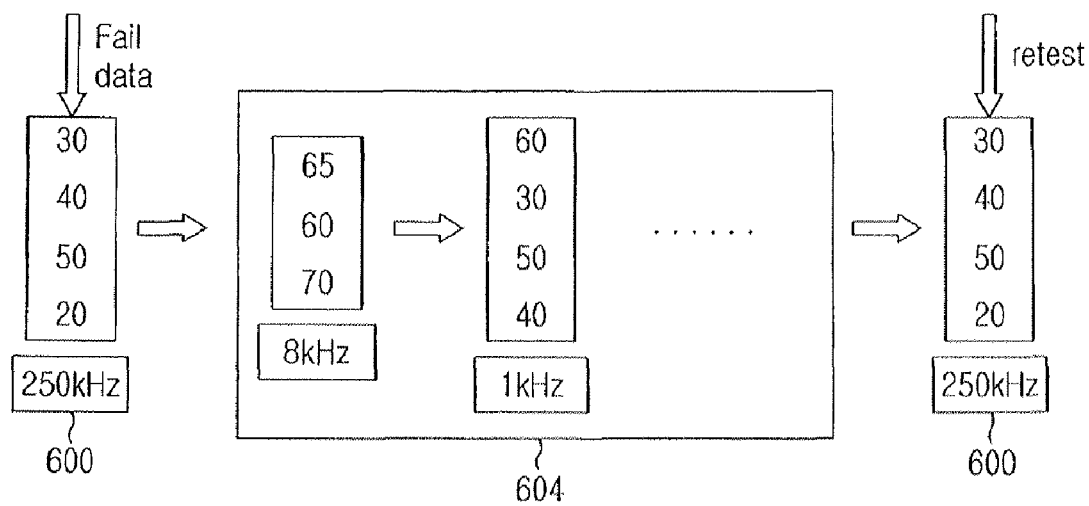
Figure 6C:
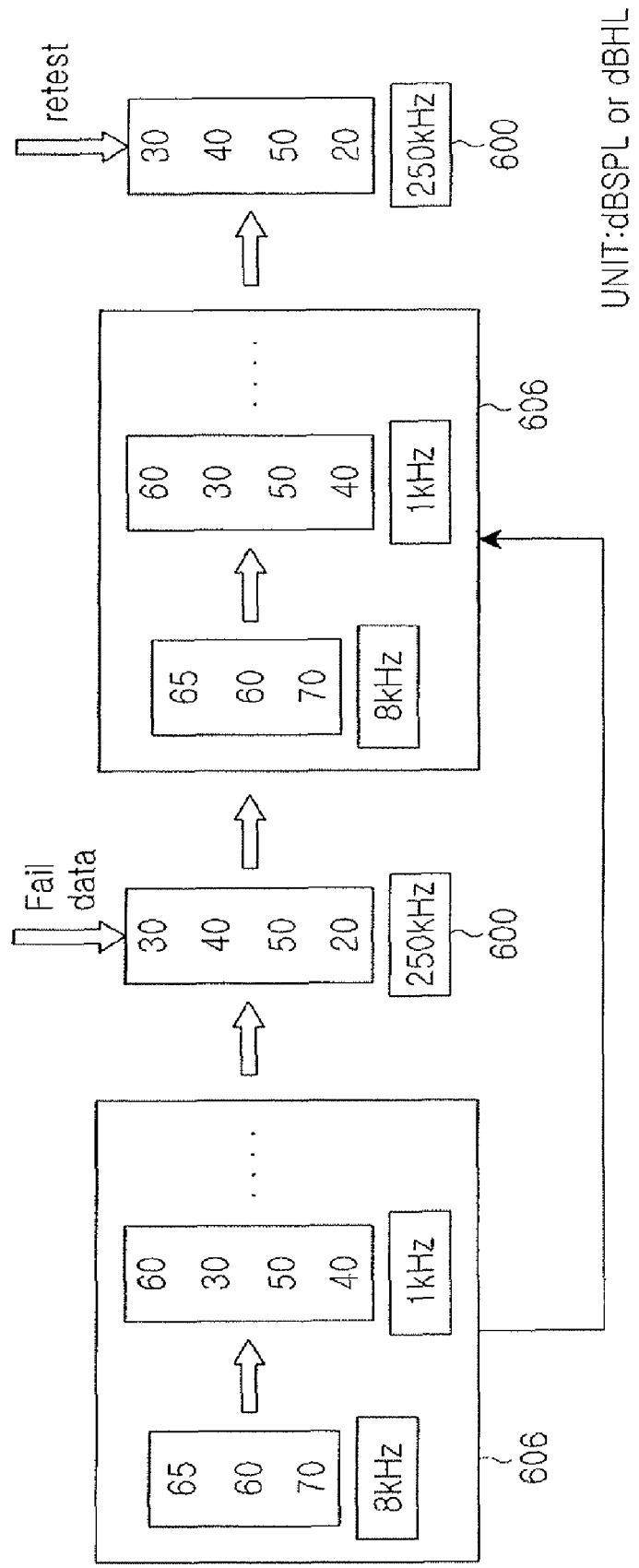

FIGS. 6A to 6C are views illustrating the process of determining an ascending threshold and a descending threshold based on a subject's incorrect response, according to an embodiment of the present general inventive concept. The incorrect response indicates that the subject's response includes a higher number than the actual number of the sound sources included in a test sound set.

The input of such an incorrect response means that the test is incorrect, and thus initialization may be required. In other words, the results of the corresponding test may be re-set to not include the information obtained during the test that drew the incorrect response. However, in a test system in which all test sound sets are not randomly selected for each test, in other words, a test system in which the test sound sets are arranged in any order before the test, if the test on one set is incorrect, it may be required that the corresponding test data be initialized and then the current test be carried out again before continuing. However, when the same test sound set is repeatedly output, the accuracy may be reduced. Also, re-output of the current test sound set is difficult because the test sound sets are in disorder. Accordingly, a G test sound set (a null test sound set) whose test result data will not be stored, may be previously stored. The G test sound set may have the same configuration as that of other test sound sets. If a test response is incorrect, the G test sound set may be output, and then a test sound set corresponding to the incorrect test response may be output again.

Referring to FIG. 6A, a test sound set 600 including 30 dBSPL, 40 dBSPL, 50 dBSPL, and 20 dBSPL sound sources in 250 k Hz is output. Then, if a response of "5" is input from a subject, which is a higher number than the actual sound sources included in the test sound set 600, a G test sound set 602 may be output, and then the test sound set 600 which drew the incorrect response may be output again. The G test sound set 602 may include a (wherein a is a natural number) test sound sets with N (wherein N is a natural number) predetermined level differences in each frequency.

In a case in which the G test sound set is not introduced, the following operation may used when the incorrect response is received. As illustrated in FIG. 6B, when the test sound set 600 is a first output test sound set after the start of the hearing test, another test sound set 604 within another frequency band may be output, and then the test sound set which drew the incorrect response, that is, the test sound set 600, may be output again. In the embodiment illustrated in FIG. 6B, the test sound set 600 which drew the incorrect response includes sound sources having a frequency of 250 k Hz, while the test sound set 604 includes sound sources having a frequency of 1 k Hz.

In a case in which the test sound set 600 is not a first output test sound set after the start of the hearing test, as illustrated in FIG. 6C, a previously output test sound set 606 may be output, and the test sound set 600 is then output again. In other words, in the event that the test sound set 600 draws an incorrect response from the subject, a test sound set 606 which was previously administered to the user without an incorrect result may be repeated, and then the test sound set 600 may be output to the subject again.

Figure 7:
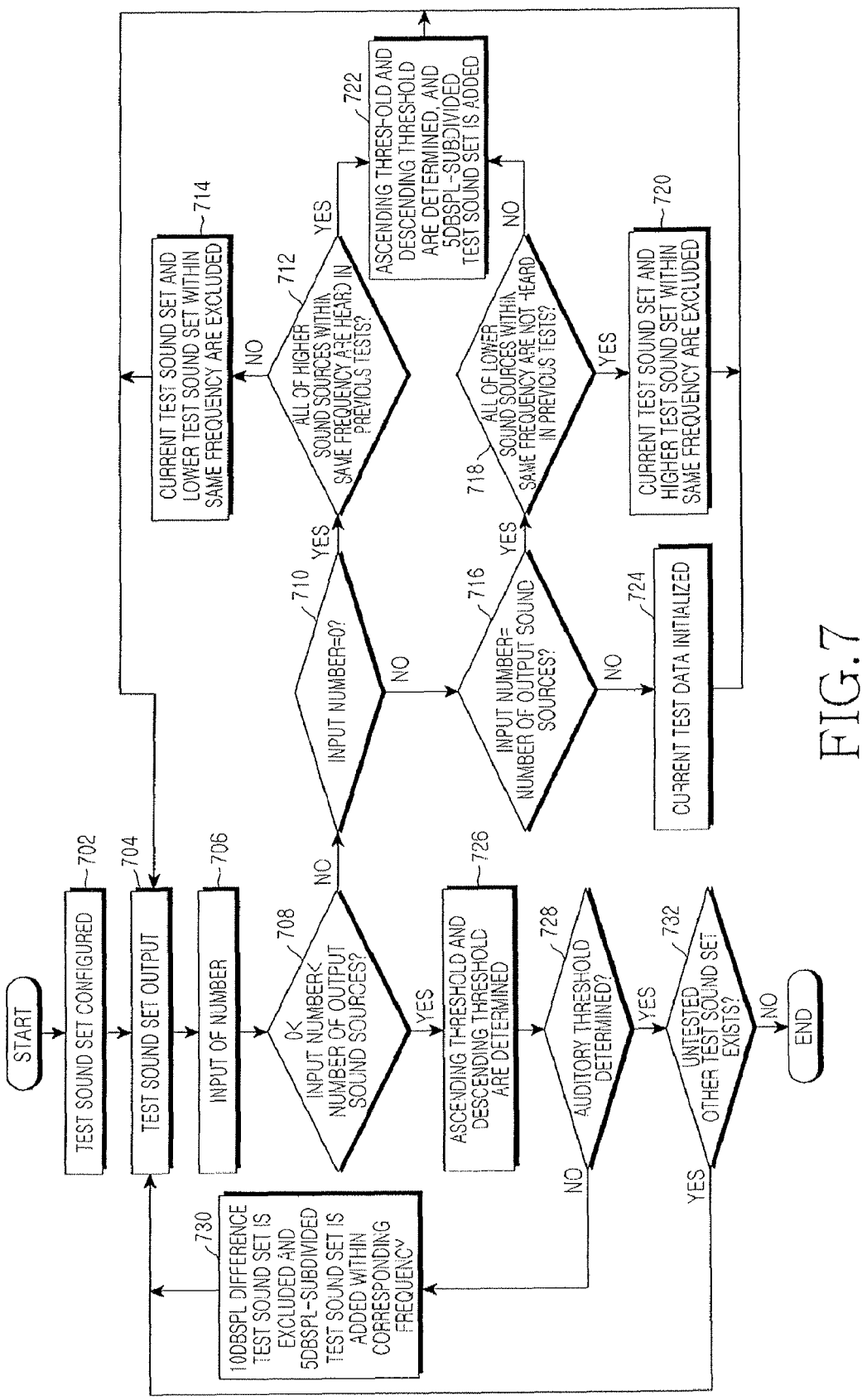
FIG. 7 is a view illustrating a hearing test process according to an embodiment of the present general inventive concept.

FIG. 7 is a view illustrating a hearing test process according to an embodiment of the present general inventive concept.

The test sound set may be previously randomly configured before the start of the hearing test. The test sound set configured before the hearing test may be arranged and output in a predetermined order, or may be randomly selected and output for each test as illustrated in FIG. 7

Referring to FIG. 7, the test sound sets may be configured before the hearing test in operation 702. When the hearing test starts, in operation 704 the hearing test device may select one test sound set from among test sound sets configured before the start, and may output sound sources of the selected test sound set in operation 704. It is assumed that the test sound sets configured at the initial stage of the test have levels with a difference of 10 dBSPL.

Additionally, the hearing test device may output the display indicating the start of the hearing test.

After the output of the test sound set, the number of sound sources (the sound source's number) is input from a subject in operation 706. In operation 708, the hearing test device may determine whether the input sound sources' number is more than 0 and less than the number of the output sound sources. If the input number is 0, it may be determined in operation 710 that the subject cannot hear the test sound set output in operation 704 or other test sound sets including sound sources with lower level volumes within the same frequency band as that of the sound sources of the test sound set output in operation 704. Then, the hearing test device may proceed to operation 712, and may determine whether the subject heard all of the sound sources with higher levels within the same frequency band as that of the previous test sound set. After the determination in operation 712, if stored results exist indicating that the subject heard all of the test sound sets having sound sources within the same frequency band with higher levels than those of the sound sources of the test sound set output in operation 704, the device may proceed to operation 722. In operation 722, the hearing test device may determine an ascending threshold and a descending threshold based on the last output test sound set, that is, the test sound set output in operation 704, may configure a test sound set with a smaller level difference (e.g., 5 dBSPL), and may proceed to operation 704 to output the newly configured test sound set. If the subject did not completely hear all of the test sound sets having the sound sources with higher levels within the same frequency band, the device may exclude the last output test sound set and the test sound sets including sound sources with lower levels within the same frequency band in operation 714, and may proceed to operation 704 to output the next test sound set.

If the determination in operation 710 is that the number input by the subject is not 0, indicating that the sound sources' number input in operation 706 is the same as the number of sound sources output in operation 704, the hearing test device may determine that the subject can hear all of the test sound set output in operation 704 and all of test sound sets including the sound sources within the same frequency band with higher levels than those of the sound sources of the test sound set output in operation 704. In this case, in operation 718, the device may determine if there is stored data from a previous test indicating that the subject did not hear all of the test sound sets including sound sources with lower levels within the same frequency as that of the test sound set output in operation 704. When there exists such a recording indicating the subject did not hear all of the test sound sets, the device may to operation 722. In operation 722, the device may determine, based on the last output test sound set, that is, the test sound set output in operation 704, an ascending threshold and a descending threshold, may configure a sub-divided test sound set with a smaller level difference (e.g., 5 dBSPL), and then may proceed to operation 704 to output the newly configured test sound set. However, when there does not exist any previous test data indicating that the subject did not hear all of the test sound sets including sound sources with lower volume levels within the same frequency, the hearing test device may proceed to operation 720, and may exclude the last output test sound set and test sound sets including sound sources with the higher levels within the same frequency, and then may proceed to operation 704 to output the following test sound set.

If it is determined, in operation 708, that the number of sound sources input in operation 706 is more than 0 and less than the number of output sound sources, the hearing test device may proceed to operation 726, and may determine an ascending threshold and a descending threshold within the test sound set output in operation 704. In operation 728, the hearing test device may determine whether it is possible to determine an auditory threshold between the determined ascending and descending thresholds. The determination of an auditory threshold depends on the uniform volume difference of the sound sources included in the test sound set output in operation 704. The auditory threshold may be determined only when the uniform volume difference is a previously determined minimum volume difference. For example, in the case where the minimum volume difference is 5 dBSPL, the auditory threshold can be determined only when neighboring sound sources have a volume difference of 5 dBSPL in the volume-based sequentially arranged sound sources of the output test sound set. Moreover, the auditory threshold can be determined only when the ascending and descending thresholds are determined within such a test sound set.

Referring to FIG. 7, when the last output test sound set does not satisfy the condition to determine an auditory threshold, the hearing test device may proceed to operation 730. In the embodiment illustrated in FIG. 7, since a basis uniform volume difference of a test sound set is assumed to be 10 dBSPL, in operation 730 the hearing test device may exclude the test sound set with a difference of 10 dBSPL from test sound sets within the corresponding frequency band, and may add a 5 dBSPL-subdivided test sound set based on the determined ascending and descending thresholds, and may proceed to operation 704 to output the added test sound set.

If it is determined in operation 728 that the test sound set output in operation 704 satisfies the condition to determine the auditory threshold, the hearing test device may determine the auditory threshold within the corresponding frequency band and proceed to operation 732. In operation 732, the hearing test device may determine if there is an untested test sound set corresponding to another frequency band. If there is an untested test sound set, the device may proceed to operation 704 and repeat the previously described operations. If it is determined in operation 732 that there are no untested test sound sets, the device may end the hearing test process.

If it is determined in operation 716 that the sound sources' number input in operation 706 is more than the number of sound sources output in operation 704, the device may proceed to operation 724, initialize the test data, and include the test sound set output in operation 704 in the following test sound sets so that it can be randomly selected and output. Otherwise, the test process may continue according to the operations illustrated in FIGS. 8A and 8B.

Figure 8A:
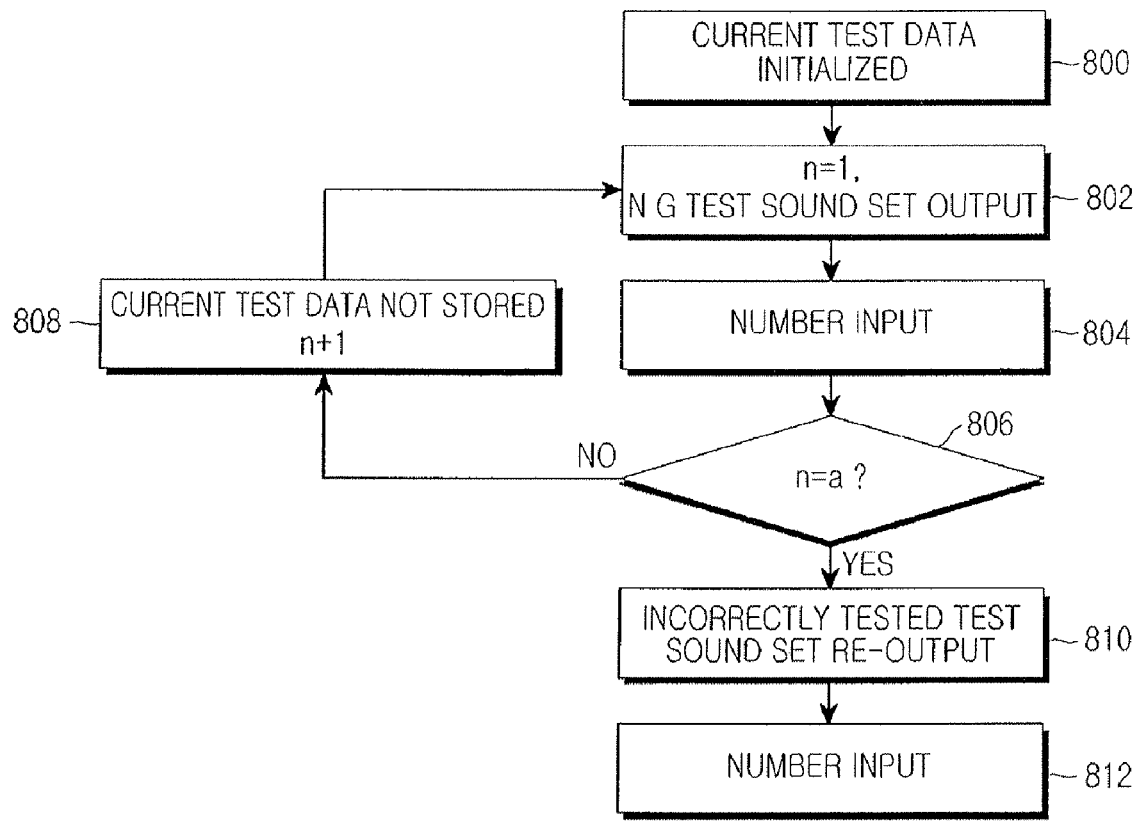
FIGS. 8A and 8B are views illustrating a hearing test process according to another embodiment of the present general inventive concept.
Figure 8B:
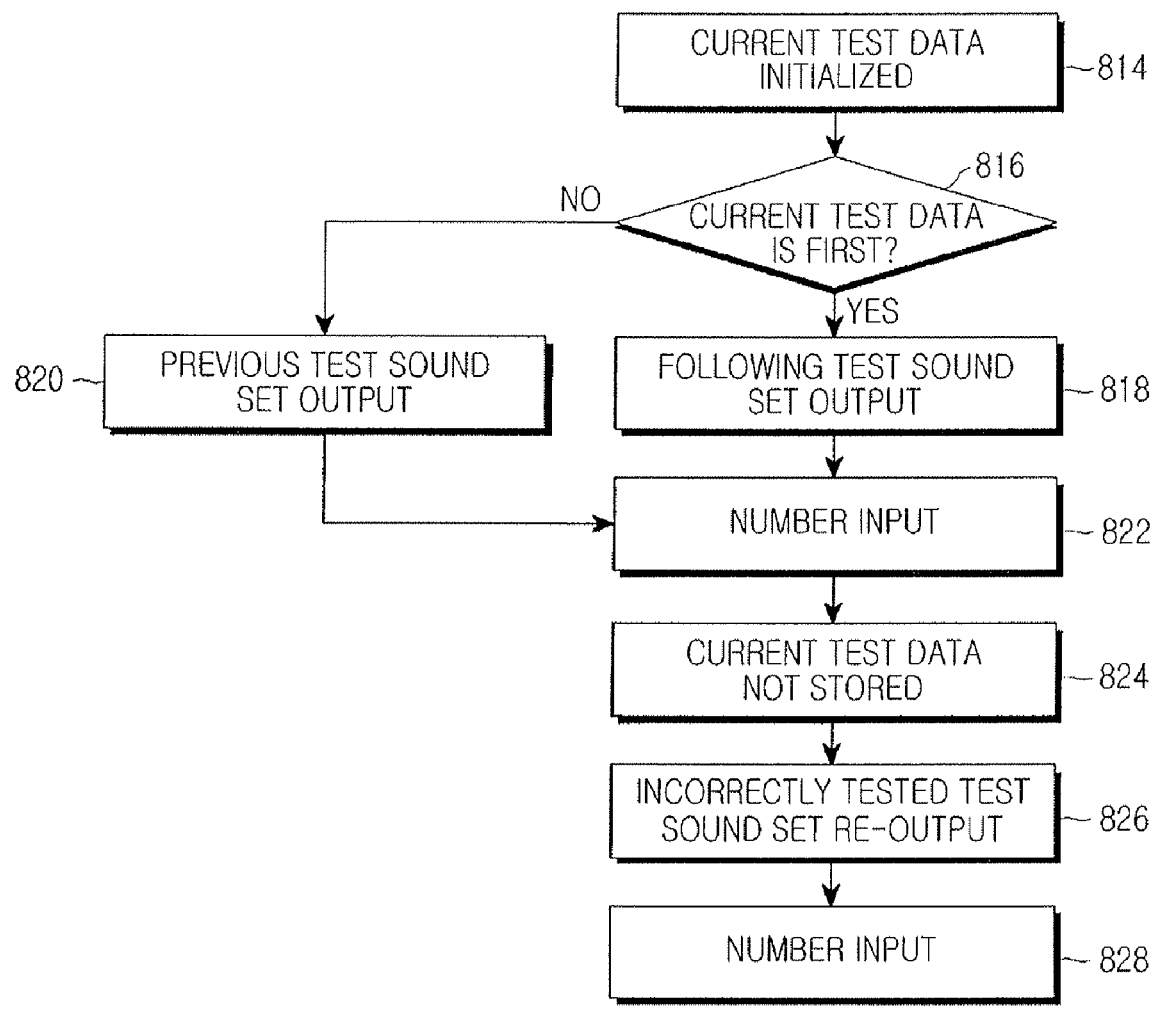

FIGS. 8A and 8B are views illustrating a hearing test process according to another embodiment of the present general inventive concept. Referring to FIG. 8A, after initializing, in operation 800, the current test data in the same manner as operation 724 of FIG. 7, the hearing test device may proceed to operation 802 and output a G test sound set. The G test sound set may include a (wherein a is a natural number) test sound sets, and the hearing test device may output the first set from among the test sound sets, and may receive the input of the sound sources' number from the subject in operation 804. Then, the device may determine whether a G test sound sets are output in operation 806. If all of the G test sound sets are not output, the device may proceed to operation 808, may not store the current test data, and may proceed to operation 802 to output the next G test sound set. If all of the G test sound sets are output, the device may proceed to operation 810 to output again the previously tested test sound set which drew the incorrect input, and may receive again the input of the sound sources' number from the subject in operation 812.

For example, if the G test sound set includes 3 test sound sets, the output of the G test sound set and the reception of the subject's number input (such as the output of the first G test sound set, and the reception of the subject's number input in response to that test sound set, and then the output of the second G test sound set, the reception of the subject's number input in response to the second test sound set, etc.) are repeated three times.

If the G test sound set is not introduced, as illustrated in FIG. 8B, in operation 814 the device may initialize the current test data after the incorrect response, and then may determine whether the incorrectly tested test sound set is the first output test sound set in the hearing test process in operation 816. If the incorrectly tested test sound set is the first output test sound set of the hearing test, the device may output the next test sound set in operation 818. On the other hand, if the test sound set drawing the incorrect response is not the first output test sound set of the hearing test, the device may output the previous output test sound set in operation 820, and may receive the input of the sound sources' number from the subject in operation 822. Then, the device does not store the test result information in operation 824, and in operation 826 may again output the test sound set which previously drew the incorrect response, and may again receive the input of the corresponding sound sources' number in operation 828. The device may then proceed with the hearing test in a similar fashion as that illustrated in FIG. 7.

The operations illustrated in FIGS. 7 through 8B may be separately carried out according to each audio frequency.

In this manner, the method and device of the present general inventive concept may reduce the subject's expectation of the volume and the output point of time of a test sound, and thus can more accurately determine an auditory threshold. Also, the present general inventive concept has an advantage in that a subject can perform the test without a tester because information regarding the start, the end, and amount of time left during the testing of a test sound set may be provided to the subject, and the subject may conduct the test by himself through a user input, such as by pressing a button. Also, the test method according to the present general inventive concept may be performed by the operation of a randomly configured system, rather than by the operation of a tester, and thus the test time may be reduced.

The present general inventive concept can also be embodied as computer-readable codes on a computer-readable medium. The computer-readable medium can include a computer-readable recording medium and a computer-readable transmission medium. The computer-readable recording medium is any data storage device that can store data as a program which can be thereafter read by a computer system. Examples of the computer-readable recording medium include read-only memory (ROM), random-access memory (RAM), CD-ROMs, DVDs, magnetic tapes, floppy disks, and optical data storage devices. The computer-readable recording medium can also be distributed over network coupled computer systems so that the computer-readable code is stored and executed in a distributed fashion. The computer-readable transmission medium can transmit carrier waves or signals (e.g., wired or wireless data transmission through the Internet). Also, functional programs, codes, and code segments to accomplish the present general inventive concept can be easily construed by programmers skilled in the art to which the present general inventive concept pertains.

Although a few embodiments of the present general inventive concept have been illustrated and described, it will be appreciated by those skilled in the art that various changes may be made in these embodiments without departing from the principles and spirit of the present general inventive concept, the scope of which is defined in the appended claims and their equivalents.

What is claimed is:

1. A method of conducting a hearing test with a hearing test device, the method comprising:
configuring multiple test sound sets comprising multiple sound sources at each included audio frequency, the sound sources, when sequentially arranged according to volume, having a uniform volume difference and a same frequency band, the uniform volume difference indicating a volume difference between neighboring sound sources;
outputting the sound sources included in one of the multiple test sound sets;
receiving a subject's input sound sources' number from a subject in response to the output sound sources; and
determining and outputting a following test sound set according to the subject's input sound sources' number one or more times, and determining an auditory threshold of the subject regarding the audio frequency of the output test sound sets based on the subject's input sound sources' number.

2. The method as claimed in claim 1, further comprising:
determining whether the subject heard or did not hear the sound sources included in the test sound set corresponding to the input sound sources' number, according to the input sound sources' number.

3. The method as claimed in claim 2, wherein the determining the auditory threshold of the subject comprises:
determining and outputting the following test sound set having a smaller uniform level difference than the uniform level difference of a previously output test sound set, within a same frequency band as the previously output test sound set, according to the subject's input sound sources' number;
receiving the subject's input sound sources' number regarding the following test sound set; and
repeatedly performing the determining and outputting of the test sound sets, and the receiving of the subject's input sound sources' number, and determining the auditory threshold of the subject accordingly.

4. The method as claimed in claim 2, wherein the determining the auditory threshold of the subject comprises:
determining an ascending threshold indicating the subject's hearable minimum volume and a descending threshold indicating the subject's unhearable maximum volume from the sound sources included in the previously output test sound set and another test sound set having the same uniform level difference as the previously output test sound set within the same frequency band, according to the subject's input sound sources' number;
determining a sound source having a mean volume between the ascending threshold and the descending threshold as the auditory threshold within the frequency band of the previously output test sound set in response to the uniform level difference of the previously output test sound set being a predetermined minimum level difference; and
determining and outputting the following test sound set comprising the ascending threshold and the descending threshold and having a smaller uniform level difference than the uniform level difference of the previously output test sound set in response to the uniform level difference of the previously output test sound set being more than the predetermined minimum level difference, and re-determining the ascending threshold and the descending threshold according to the subject's input sound sources' number regarding the following test sound set.

5. The method as claimed in claim 4, wherein if the subject's input sound sources' number is less than a number of the sound sources included in the test sound set corresponding to the input sound sources' number, and more than 0, the ascending threshold and the descending threshold are determined from the sound sources included in the corresponding test sound set.

6. The method as claimed in claim 4, wherein if the subject's input sound sources' number is 0, and it is determined that the subject heard all of the sound sources having higher volumes in the same frequency band than the sound sources included in the test sound set corresponding to the subject's input sound sources' number of 0, the determining the auditory threshold of the subject further comprises:

determining, as the descending threshold, a highest volume sound source from the sound sources included in the test sound set corresponding to the subject's input sound sources' number of 0; and determining, as the ascending threshold, a sound source having a higher volume than the descending threshold by a uniform volume of the test sound set corresponding to the sound sources' number of 0.

7. The method as claimed in claim 4, wherein if the subject's input sound sources' number equals a number of the sound sources included in the test sound set corresponding to the sound sources' number, and it is determined that the subject did not hear all of the sound sources having smaller volumes in the same frequency band than the volumes of sound sources included in the test sound set corresponding to the subject's input sound sources' number, the determining the auditory threshold of the subject further comprises:

determining, as the ascending threshold, a lowest volume sound source from the sound sources included in the test sound set corresponding to the sound sources' number; and determining, as the descending threshold, a sound source having a lower volume than the ascending threshold by a uniform volume of the test sound set corresponding to the sound sources' number.

8. The method as claimed in claim 4, wherein the determining the auditory threshold of the subject further comprises:

outputting a predetermined null test sound set in response to the subject's input sound sources' number being more than a number of the sound sources included in the test sound set corresponding to the sound sources' number; and re-outputting the test sound set corresponding to the sound sources' number.

9. The method as claimed in claim 5, wherein the determining the auditory threshold of the subject further comprises:

determining and outputting a test sound set comprising the ascending threshold and the descending threshold, and having a smaller uniform level difference than the uniform level difference of the previously output test sound set, as the following test sound set in response to a volume difference between the sound sources corresponding to the ascending threshold and the descending threshold being more than the minimum volume difference, and then re-determining the ascending threshold and the descending threshold according to the subject's input sound sources' number regarding the following test sound set.

10. The method as claimed in claim 1, wherein output durations and output points of time of the respective sound sources included in the test sound sets are randomly determined.

11. The method as claimed in claim 1, wherein a test start point of time and a test end point of time are displayed on a screen in response to the test sound sets being output.

12. The method as claimed in claim 1, wherein a number of the sound sources included in each of the test sound sets is randomly determined.

13. The method as claimed in claim 1, further comprising:
receiving an initial hearing level of the subject;
determining a volume level for each audio frequency based on the initial hearing level of the subject; and
initially configuring the test sound sets with the determined volume level for each audio frequency.

14. A method of conducting a hearing test, the method comprising:

outputting one or more previously configured test sound sets to a subject, each or the one or more previously configured test sound sets including multiple sound sources;

receiving a subject's input of a number of sound sources from a subject in response to the output one or more previously configured test sound sets; and determining an auditory threshold of the subject according to the subject's input, wherein at least one successive test sound set is configured according to a subject's input of a number of sound sources in response to outputting of a current test sound set.

15. The method of claim 14, wherein the previously configured test sound sets include varying numbers of sound sources in a common frequency band and the sound sources in any one of the previously configured test sound sets have a uniform volume difference when sequentially arranged according to volume.

16. The method of claim 14, wherein sound sources in the successive test sound set have a reduced uniform volume difference compared to the uniform volume difference of the sound sources in the current test sound set.

* * * * *